United States Patent [19]

Pelosi, Jr. et al.

[11] 4,066,670
[45] Jan. 3, 1978

[54] N-DIMETHYLAMINOPROPYL-5-(2-NITROPHENYL)-2-FURANCARBOXIMIDAMIDE DIHYDROCHLORIDE MONOHYDRATE

[75] Inventors: Stanford S. Pelosi, Jr.; Ronald E. White; George C. Wright; Chia Nien Yu, all of Norwich, N.Y.

[73] Assignee: Morton-Norwich Products, Inc., Norwich, N.Y.

[21] Appl. No.: 765,621

[22] Filed: Jan. 25, 1977

[51] Int. Cl.$^2$ .................................... C07D 307/68
[52] U.S. Cl. ........................... 260/347.7; 424/285
[58] Field of Search ................................ 260/347.7

[56] References Cited

U.S. PATENT DOCUMENTS 3,906,010   9/1975   Pelosi et al. ................. 260/347.7 X Primary Examiner—Richard L. Raymond
Attorney, Agent, or Firm—Anthony J. Franze

[57] ABSTRACT

N-Dimethylaminopropyl-5-(2-nitrophenyl)-2-furancarboximidamide dihydrochloride monohydrate is useful as an anti-inflammatory agent.

1 Claim, No Drawings

N-DIMETHYLAMINOPROPYL-5-(2-NITROPHENYL)-2-FURANCARBOXIMIDAMIDE DIHYDROCHLORIDE MONOHYDRATE

This invention relates to the compound N-dimethylaminopropyl-5-(2-nitrophenyl)-2-furancarboximidamide dihydrochloride monohydrate of the formula:

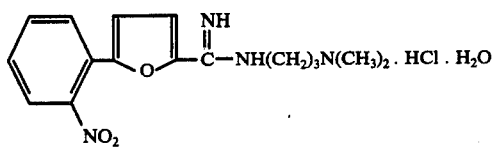

and a method for its preparation.

This compound possesses pharmacologic activity. It is particularly useful as an anti-inflammatory agent as evidenced by its ability to inhibit edema induced in rats by the administration of carrageenin. Thus, when administered at a dose of 200 mg/kg suspended in a vehicle such as aqueous methyl cellulose per os to rats receiving carrageenin, edema associated with that substance is inhibited by 69% [Winter et al., P.S.E.B.M. 111:544].

This compound is preferably prepared in accordance with the following example:

A mixture of 5-(2-nitrophenyl)-2-furonitrile (92 g, 0.43 mole) and anhydrous methanol (1000 ml) was heated to 55° and sodium methoxide (1.5 g) was added. The steam bath was removed, the solution was stirred for two hours and stored overnight at room temperature. The solution was poured into ice water (1000 ml) and stirred for one hour. The product was collected by filtration and air dried to yield 91 g (86%) of methyl 5-(2-nitrophenyl)-2-furancarboximidate. A sample was recrystallized from isopropanol, m.p. 107°-108°.

Anal. Calcd. for $C_{12}H_{10}N_2O_4$: C, 58.54; H, 4.09; N, 11.38. Found: C, 58.56; H, 3.87; N, 11.26.

A mixture of the above compound (29 g, 0.12 mole), ethanol (300 ml), and dimethylaminopropylamine (12.2 g, 0.12 mole) was stirred for 15 hours at room temperature and then refluxed for seven hours. The mixture was stripped of solvent under reduced pressure, the product extracted with hot cyclohexane, stirred over Darco and filtered. The filtrate was reduced in volume to 150 ml under reduced pressure, cooled, and the cyclohexane was decanted. The product was dissolved in anhydrous ether and adjusted to pH 2 with ether/HCl. The product was collected by filtration and recrystallized from isopropanol to yield 8 g (16%) of N-dimethylaminopropyl-5-(2-nitrophenyl)-2-furancarboximidamide dihydrochloride monohydrate, recrystallized from methanol, m.p. 204°-209°.

What is claimed is:

1. The compound N-dimethylaminopropyl-5-(2-nitrophenyl)-2-furancarboximidamide dihydrochloride monohydrate.